United States Patent [19]

Bevan et al.

[11] Patent Number: 5,725,582
[45] Date of Patent: Mar. 10, 1998

[54] SURGICAL IMPLANTS

[75] Inventors: David Robin Bevan, Gower; Richard William Porter, Doncaster; John Anthony Norman Shepperd, Telham, nr. Battle; Peter William Phillips, Evesham, all of Great Britain

[73] Assignee: Surgicraft Limited, Worchestershire, Great Britain

[21] Appl. No.: 387,710

[22] PCT Filed: Aug. 18, 1993

[86] PCT No.: PCT/GB93/01746

§ 371 Date: Aug. 8, 1995

§ 102(e) Date: Aug. 8, 1995

[87] PCT Pub. No.: WO94/04088

PCT Pub. Date: Mar. 3, 1994

[30] Foreign Application Priority Data

Aug. 19, 1992 [GB] United Kingdom ............ 9217578

[51] Int. Cl.$^6$ .................................................. A61F 2/44
[52] U.S. Cl. ....................... 623/17; 623/13; 606/61; 24/129 W
[58] Field of Search ............... 623/13, 17; 606/60, 606/61; 24/129 W, 115 A, 265 A, 481, 482

[56] References Cited

U.S. PATENT DOCUMENTS

| | | | |
|---|---|---|---|
| 3,705,444 | 12/1972 | Wernsing | 24/115 A |
| 3,857,396 | 12/1974 | Hardwick | 24/115 A |
| 4,059,866 | 11/1977 | Rohland | 24/115 A |
| 4,570,618 | 2/1986 | Wu | 606/61 |
| 4,790,303 | 12/1988 | Steffee . | |
| 5,092,866 | 3/1992 | Breard et al. . | |
| 5,116,340 | 5/1992 | Songer et al. . | |
| 5,387,213 | 2/1995 | Breard | 623/17 |
| 5,395,370 | 3/1995 | Müller | 606/61 |
| 5,423,820 | 6/1995 | Miller | 24/129 W |
| 5,454,812 | 10/1995 | Lin | 606/61 |
| 5,456,722 | 10/1995 | McLeod | 623/17 |
| 5,476,565 | 12/1995 | Preissman | 606/61 |
| 5,496,318 | 3/1996 | Howland | 606/61 |

FOREIGN PATENT DOCUMENTS

| | | | |
|---|---|---|---|
| 322334 | 6/1989 | European Pat. Off. | 623/17 |
| 2662073 | 11/1991 | France | 623/17 |
| 9300261 | 2/1993 | United Kingdom . | |

*Primary Examiner*—Michael J. Milano
*Attorney, Agent, or Firm*—Trexler, Bushnell, Giangiorgi & Blackstone, Ltd.

[57] ABSTRACT

A surgical implant (20) comprises a hank formed from a single strand (21) of flexible biocompatible material (such as polyester) with at least one bight (22) at each end of the hank and a tail (25) extending from one end, and a crimpable sleeve-like element (26) encircling the overlapping end lengths (27) of the strand. The implant (20) is shown in use for the stabilization of the spine, the bights (22) being applied to hooking members (30, 39) engaged respectively with the lamina (47) of one vertebra (24) and the spinous process (23) of an adjacent vertebra, the strand material (21) being tensioned by pulling the tail (25) before crimping the sleeve-like element (26).

16 Claims, 6 Drawing Sheets

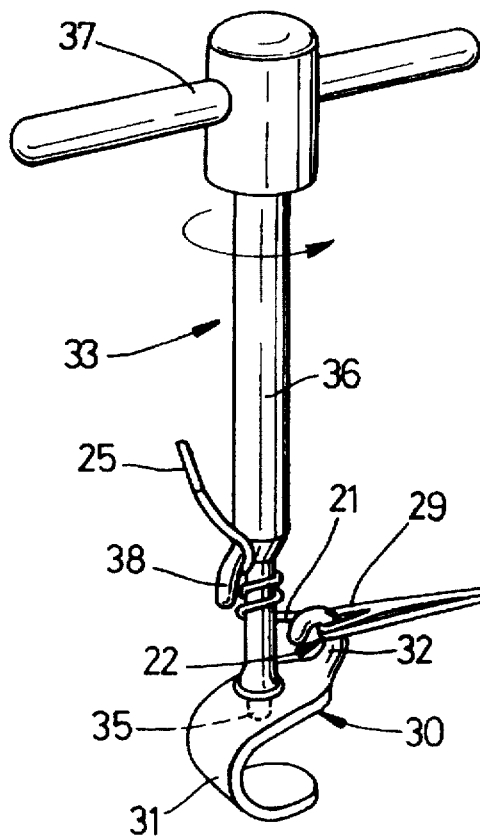
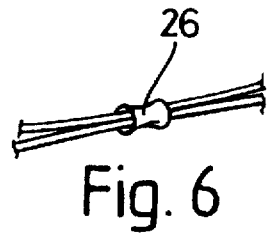
Fig. 6
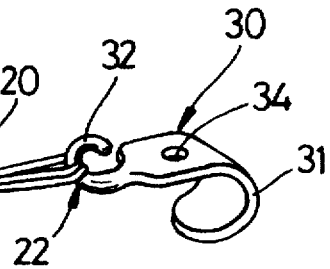
Fig. 5
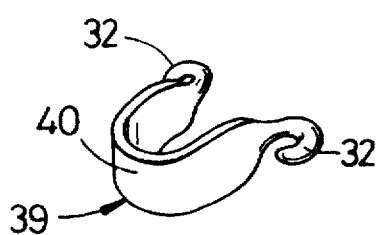
Fig.7
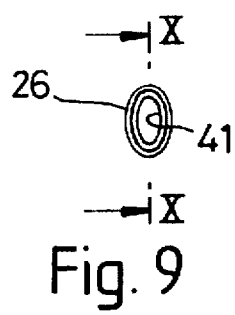
Fig. 9
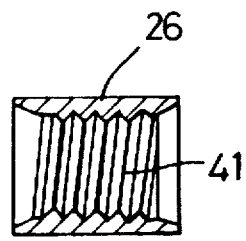
Fig.10
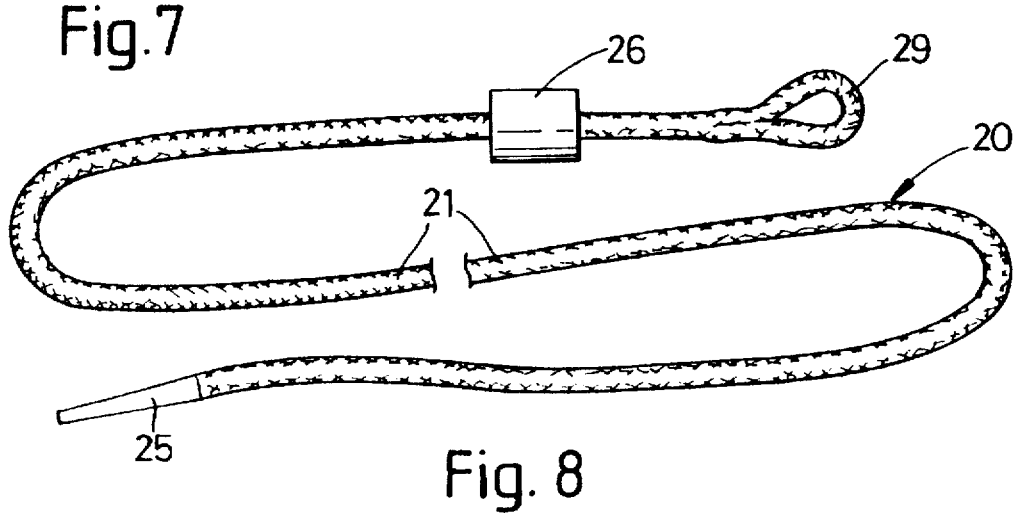
Fig. 8

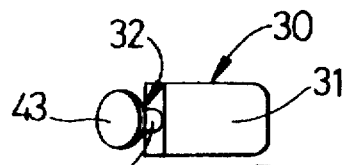
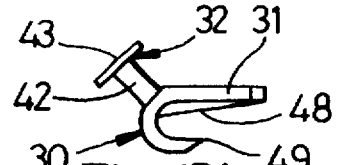
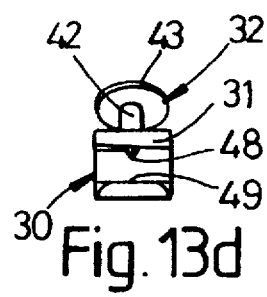
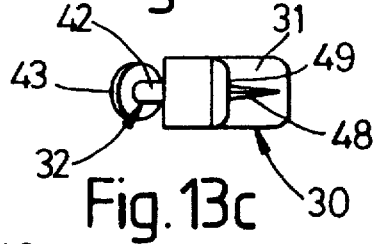
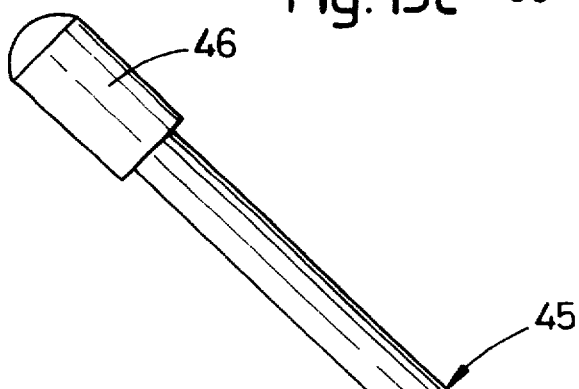
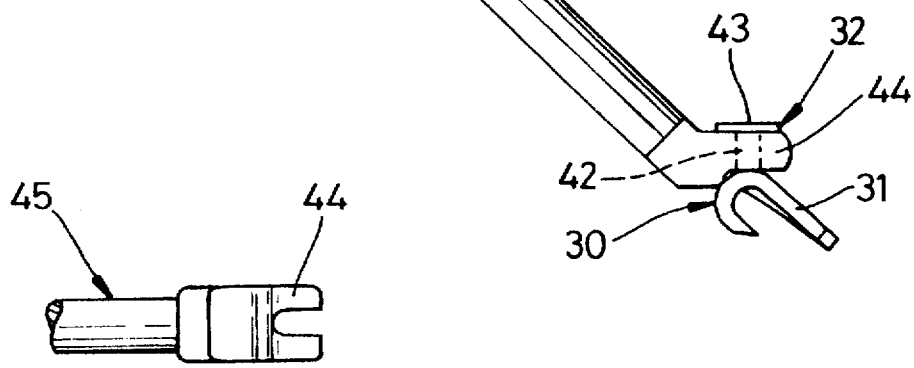

SURGICAL IMPLANTS

BACKGROUND OF THE INVENTION

This invention relates to surgical implants, etc., more particularly—but not exclusively—for the stabilization of the spine, but also applicable to other indications, such as the replacement or augmentation of knee or ankle ligaments, and also possibly applicable to the reduction of fractured bones.

Various forms of spinal stabilization are in use, including fixation devices such as Harrington, Hartshill (see EP-A-0 146 347 and EP-A-0 269 268 both of Surgicraft Limited), Luque, and Knodt, which comprise solid rods hooked on to the vertebrae or held thereto by wires.

More recently there have been introduced flexible stabilisation systems, such as inextensible strips between pedicle screws (see Burton U.S. Pat. No. 4,743,260 and F. H. Breard and H. Graf EP-A-0 381 588) or inextensible bands of predetermined lengths round pedicle screws (see also EP-A-0 381 588).

However, in order to avoid failure of these anchorages in pedicles it has been proposed (in EP-A-0 381 588) to loop inextensible flexible members directly round the spinous processes; Senegas has an inextensible member wound in a figure of eight or multiples thereof round the spinous processes and through spacers therebetween, while EP-A-0 322 334 of COTE S.A.R.L. (granted to CREMASCOLI FRANCE) has semi-elastic flat lacing looped round the spinous processes and in between passed through small tubular cushions of the same material.

The winding or looping of flexible members, whether inextensible or semi-elastic, round the spinous processes and through spacers or cushions is a time-consuming operation, and it is also difficult to tension the flexible members to adjust the load between vertebrae spanned by the flexible members, because of friction of the flexible members with themselves and with the bones and spacers or cushions.

SUMMARY OF THE INVENTION

One object of the present invention is to provide a surgical implant that can be quickly and surely applied, particularly for spinal stabilization but also for ligament augmentation or replacement or for reduction of fractured bones, and that can be easily tensioned to adjust the load between vertebrae spanned.

A secondary object of the invention is to adapt the surgical implant for alternative methods of engagement with the spine or with other bones in the body.

According to one aspect of the present invention, a surgical implant comprises a hank formed from a single strand of flexible biocompatible material with at least one bight at each end of the hank and a tail extending from at least one end, and at least one crimpable sleeve-like element encircling at least the overlapping end lengths of the strand.

With this simplest form, the two bights can be quickly and surely applied one over each of two spinous processes (or anchoring means such as pedicle screws secured in two vertebrae), any slack being taken up by pulling the tail, further pulling of which makes use of the purchase of the looped strand material to adjust the load between the vertebrae, then the crimpable sleeve-like element is squeezed (using any suitable, e.g., proprietary crimping tool) on to the lengths of strand passing therethrough secure the strand in its tensioned state.

The at least one crimpable sleeve-like element may encircle all the strands of the hank intermediate its ends, or only all the lengths of strand at one side of the hank, and more than one crimpable sleeve-like element may be applied to the hank.

For other indications, such as ligament augmentation or replacement, the bights are simply applied over suitable heads of anchorages in the relevant bones.

Conveniently, the at least one bight at one end of the hank comprises an eye formed at the end of the strand material remote from the tail, while the at least one bight at the other end of the hank is formed by the strand material looping from the corresponding end of the crimpable sleeve-like element. It will be evident that the eye will be of a size adequate to fit over a spinous process or the head of a pedicle screw or other anchorage.

The hank may consist of a plurality of loops of the single strand of flexible biocompatible material, so as to increase the purchase when pulling the tail to adjust the load between vertebrae or other bone parts. Thus the hank will have at each end a corresponding plurality of coincident bights.

In order to adapt the surgical implant for alternative engagement with the lamina or transverse processes on either side of the spine and/or to distribute the load over a greater edge area of the spinous processes (or the lamina or transverse processes) than is afforded to the strand material when applied directly thereto, the surgical implant according to another aspect of the present invention also comprises a pair of hooking members, each having a broad flat hook portion for engaging one part of the spinal column, integrated with an oppositely directed and reverse facing round hook portion engageable with the bight or bights at one end of the hank. For symmetrical loading of vertebrae, two implants in accordance with the invention and each comprising a hank, a crimpable sleeve-like element, and two hooking members, all as defined above, may be applied to the lamina or transverse processes at both sides of the spine. Alternatively, two hooking members, each in the form of a broad flat yoke with a round hook portion integrated with and oppositely directed to each end of the yoke, are combined with two hanks and two crimpable sleeve-like elements as defined above, the yokes being hooked on to spinous processes and the hanks lying one to each side of the spinous processes. Again, one yoke may be applied to the spinous process of one vertebra, and two hooking members, as defined above, may be applied to the lamina at both sides of the spinous process of other vertebra, and combined with two hanks and two crimpable sleeve-like elements as defined above, the bights of the hanks being applied to respective round hook portions on the yoke and the corresponding hooking members.

At least one of the hooking members preferably has abutment means for a tensioning tool for pulling the tail of the strand material, which abutment means may take the form of a hole (or a spigot) located between the flat and round hook portions (or between the yoke and the round hook portions).

Each round hook portion is preferably formed by a bollard having a cylindrical body and a flat circular head, which aids retention of an eye at one end of the strand material. The bollard is also conveniently engageable by a forked end of an applicator tool having a striking portion at the other end; and the flat circular head of the bollard may also serve as a spigot for engagement by a socket in a tensioning tool.

A selection of hooking members is preferably made available with a variety of widths and radii of the broad flat hook portions and/or of the yoke portion, so that the surgeon can select hooking members appropriate to the size and shape of parts of the spinal column.

The hooking members, when used on the spine, may be attached to the cranial or caudal border of the lamina, the cranial base of the transverse processes, or the caudal edge of the sacral foramen.

The insides of the broad flat hook portions and/or of the broad flat yokes are preferably provided with sharp-ridged ribs extending in the direction of application of the hooking members, to enhance the grip on engaged bone parts; and a leading end of each broad flat hook portion is preferably provided with a chisel edge, to effect some shaving of an engaged bone part, if necessary, to achieve a good fit.

The strand material may be made of polyester or any other suitably strong flexible inert or biocompatible material, and the crimpable sleeve-like element may be made from any suitably ductile inert material.

The inside of the crimpable sleeve-like element is preferably provided with circumferentially extending ribs, to enhance the grip on the strand material; thus, this element may be conveniently manufactured as an initially cylindrical and, preferably, internally screwthreaded sleeve, which is then flattened slightly, so as to accommodate a pair of overlapping end lengths of strand material in an element having minimal cross-sectional dimensions.

The hooking members may be made from any suitable implant material (e.g., stainless steel, titanium, ceramic) and may be coated with hydroxyapatite to encourage ingrowth of bone tissue, which will assist in reducing edge loading, while a plurality of turns of strand material in the hank will encourage ingrowth of body tissue.

According to a further aspect of the present invention, of independent significance, a capstan for tensioning a flexible surgical strand comprises a shank with a co-axial spigot or socket at one end for engagement with a hole in or spigot on a surgical implant, handgrip means at the other end of the shank for rotating the capstan after engagement with the spinal implant, and means on the shank (such as a cleat thereon or a notch or aperture therein), for securing a flexible surgical strand to the shank for winding thereon upon rotation of the capstan.

The handgrip means may comprise a crossbar secured to the shank, or it may comprise a knurled knob, which may be coupled to the shank through a torque-setting device, for indicating or limiting the load applied to a flexible surgical strand secured to the shank as aforesaid.

According to yet another aspect of the present invention, of independent significance, a method of spinal stabilisation comprises securing to two parts of the spinal column respective bights at the ends of a hank formed from a single strand 6f flexible biocompatible material having at least its overlapping end lengths encircled by at least one crimpable sleeve-like element, with a tail of the strand extending from an end of the hank, pulling the tail to take up slack in the hank and tension the strand, squeezing the crimpable sleeve-like element on to the lengths of strand passing therethrough to secure the strand in its tensioned state, and cutting off excess strand material.

The bights may be secured to two vertebrae by applying them one over each of the respective spinous processes, or they may be applied over the heads of pedicle screws screwed into the vertebrae or other parts of the spinal column.

Alternatively, hooking members, each having a broad flat hook portion integrated with an oppositely directed and reverse facing round hook portion, are applied one to each of two vertebrae, with the respective flat hook portion engaged with the spinous process or to the lamina or transverse process at one side of the spine, then engaging the bights of the hank with the respective round hook portions of the hooking members, whereafter the tail of the strand can be pulled, the crimpable sleeve-like element squeezed, and excess strand material cut off, as described above.

A similar combination of hooking members, hank and crimpable sleeve-like element may be applied similarly at the other side of the spine to achieve symmetrical loading of the vertebrae.

Again, hooking members, each having a broad flat yoke with a round hook portion integrated with and oppositely directed to each end of the yoke, are applied one to each of two spinous processes, with the respective yoke portion engaged with a spinous process, the round hook portions then being engaged by respective bights of a pair of hanks each of which is formed from a single strand of material, as aforesaid, with a tail and an encircling crimpable sleeve-like element, the tails being pulled, the crimpable sleeve-like elements squeezed, and excess strand material cut off, as described above, to achieve symmetrical loading.

Yet again, a hooking member having a broad flat yoke with a round hook portion integrated with and oppositely directed to each end of the yoke may be applied to the spinous process of one vertebra, and two hooking members each having a broad flat hook portion integrated with an oppositely directed and reverse facing round hook portion are applied to the lamina at both sides of the spinous process of another vertebra, the respective round hook portions of the yoke and the corresponding hooking members engaged with the lamina then being engaged by respective bights of a pair of hanks each of which is formed from a single strand of material, as aforesaid, with a tail and an encircling crimpable sleeve-like element, the tails being pulled, the crimpable sleeve-like elements squeezed, and excess strand material cut off as described above, to achieve symmetrical loading.

A tensioning tool, such as the capstan described above, may be applied to one of the hooking members, engaged with the tail (or each of the tails) and operated (e.g., rotated) to tension the strand (or each strand) before squeezing of the (or each) crimpable sleeve-like element.

BRIEF DESCRIPTION OF THE DRAWINGS

Embodiments of the invention and manner of application thereof will now be described, by way of example only, with reference to the accompanying drawings in which:

FIG. 5 is a perspective view of a basic concept for a surgical implant in accordance with the invention provided with hooking members, one of which is engaged by a tensioning tool;

FIG. 6 is a fragmentary perspective view showing the crimpable sleeve-like element of FIG. 5 after crimping on to the lengths of strand passing through it;

FIG. 7 is a perspective view of alternative form of hooking member to those shown in FIG. 5;

FIG. 8 is a plan view of components of a preferred form of surgical implant in accordance with the invention;

FIG. 9 is an end view of the crimpable sleeve-like element of FIG. 8;

FIG. 10 is an enlarged section taken from the line X—X of FIG. 9;

FIGS. 13(a), (b), (c) and (d) are respective plan, side, underneath and end views of one of the hooking members shown in FIGS. 11 and 12;

FIG. 14 is a side elevation of a tool for use in driving into place a hooking member as in FIGS. 13(a) to (d) and shown engaged therewith;

FIG. 15 is a fragmentary underneath view of the lower end of the tool of FIG. 14, without the hooking member;

DETAILED DESCRIPTION OF THE ILLUSTRATED EMBODIMENTS

Figure 1:
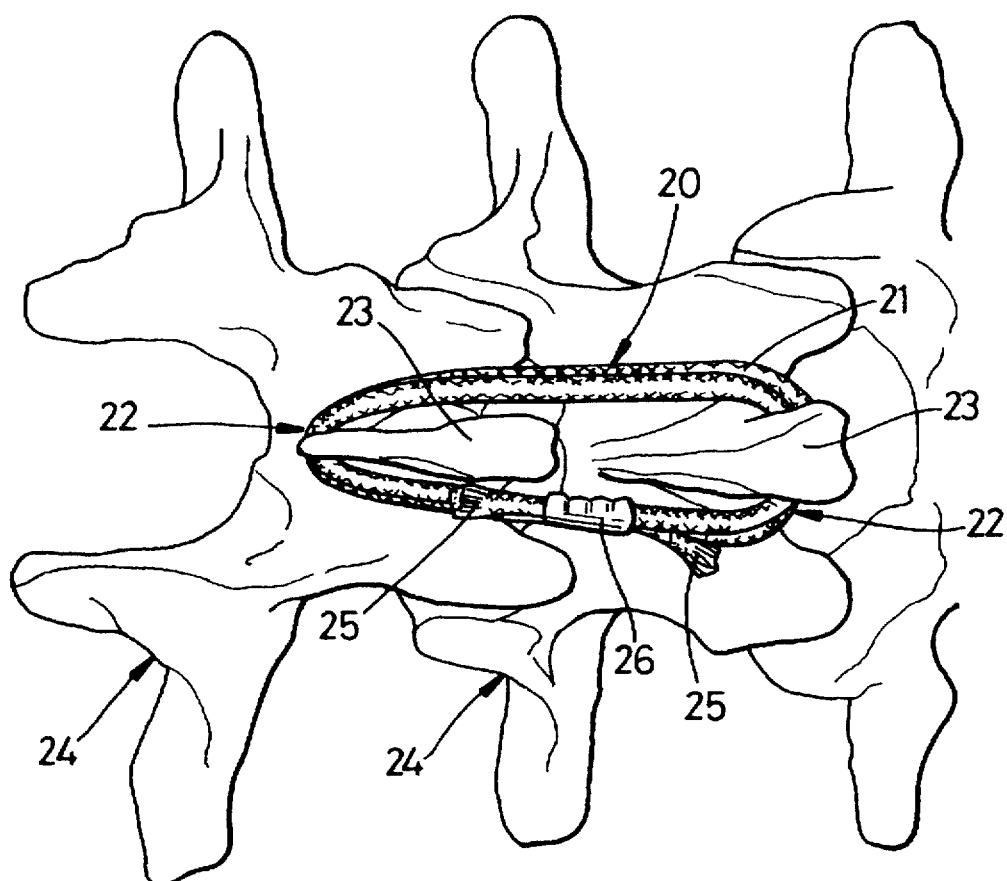
FIG. 1 is a plan view of one of the simplest forms of surgical implant in accordance with the invention shown applied to the spinous processes of adjacent vertebrae.
Figure 2:
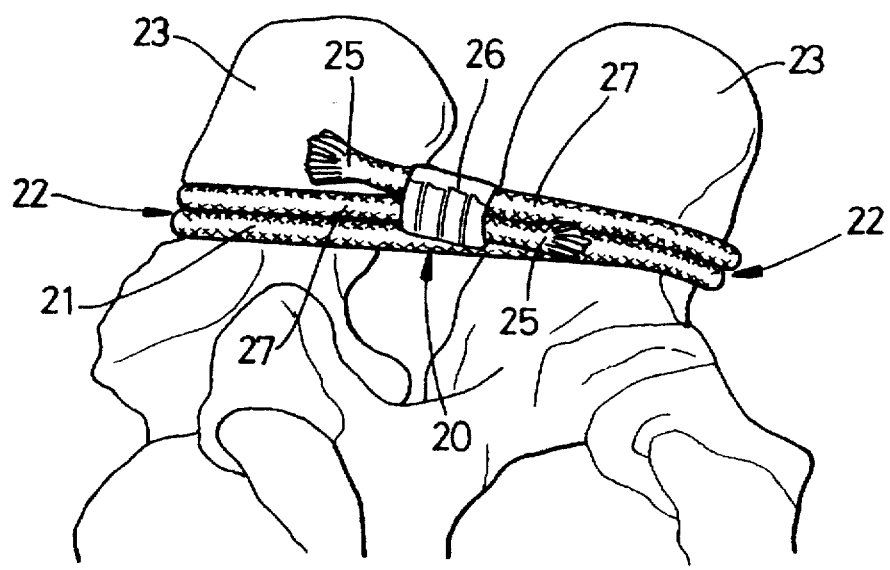
FIG. 2 is a side elevation of parts of FIG. 1, as seen from the lower side of FIG. 1.

In FIGS. 1 and 2, a surgical implant 20 comprises a hank formed from a single strand 21 of flexible biocompatible material with bights 22 at both ends, applied over each of two spinous processes 23 on adjacent vertebrae 24 with tails 25 projecting from a crimpable sleeve-like element 26 encircling the overlapping end lengths 27 of the strand, the element 26 being shown as having been crimped to secure the strand 21 after tensioning by pulling the tails 25 in opposite directions.

Figure 3:
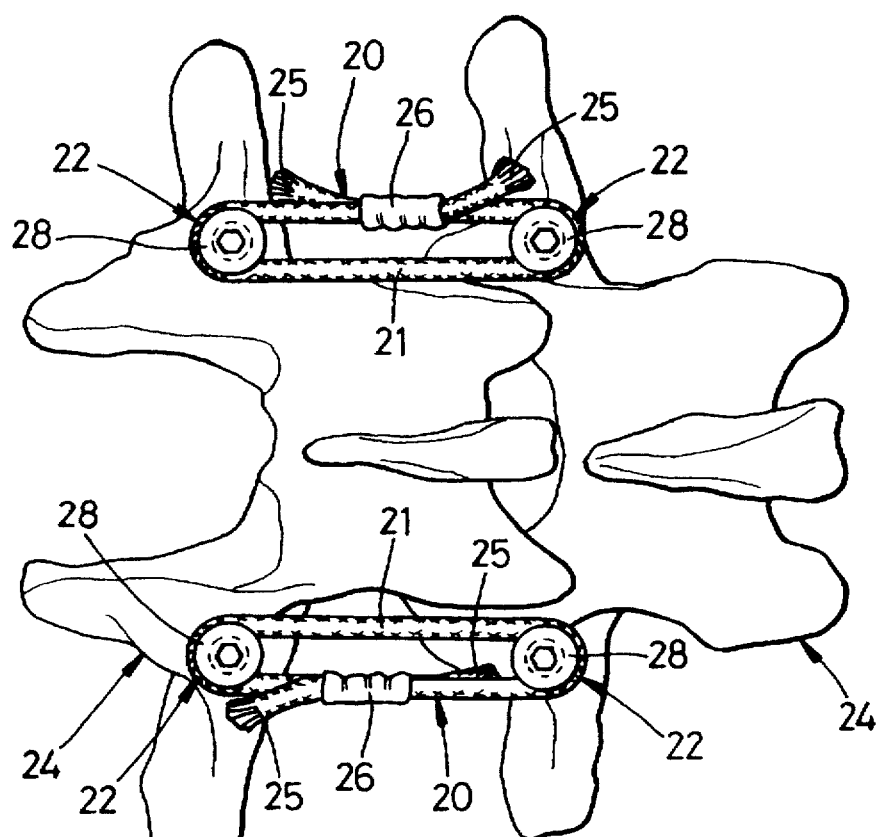
FIG. 3 corresponds to FIG. 1 but shows two of the simplest forms of implant applied to pairs of pedicle screws secured in both sides of a pair of adjacent vertebrae.
Figure 4:
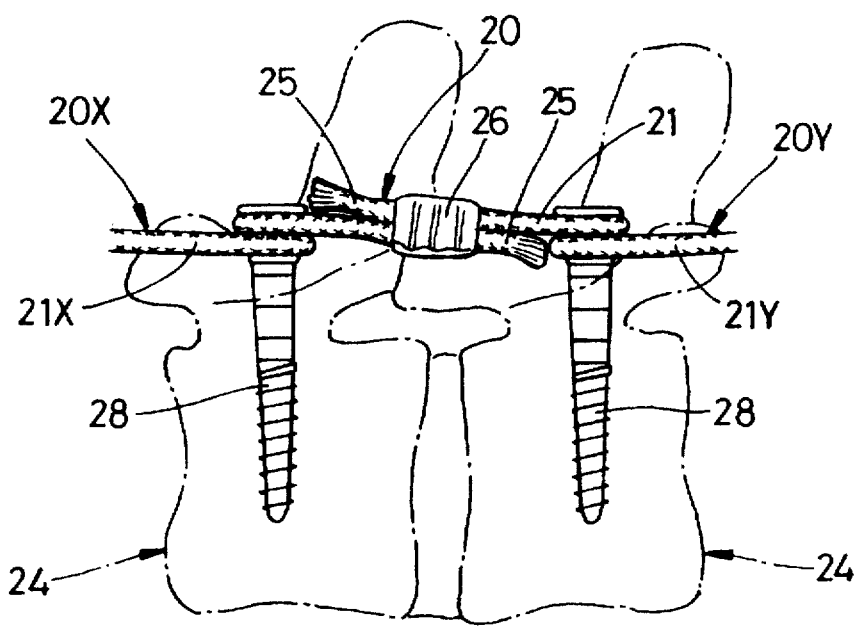
FIG. 4 is a side elevation of one of the implants of FIG. 3 and its associated pedicle screws, with an indication (in chain-dotted lines) of the pair of adjacent vertebrae, and with an indication how further similar implants can extend from those pedicle screws.

In FIG. 3, two similar implants 20 are applied to pairs of pedicle screws 28 secured in both sides of a pair of adjacent vertebrae 24, the crimpable sleeve-like elements 26 being shown as having been crimped after tensioning the strands 21 to provide symmetrical loading of the vertebrae. In FIG. 4, strands 21X, 21Y of further implants 20X, 20Y are indicated as extending to further adjacent vertebrae which are not shown or indicated.

The strand 21 shown in FIG. 5 has one bight at one end of the hank comprising an eye 29 formed at the end of the strand material remote from the tail 25, and the hank consists of a plurality of loops with all the lengths of strand between the bights 22 encircled by the crimpable sleeve-like element 26. Hooking members 30 each have a broad flat hook portion 31 for engaging one part of the spinal column, e.g., the lamina or transverse processes (not shown) on one side of the spine and to distribute the load over a greater edge area thereof, and an oppositely directed and reverse facing round hook portion 32 engaged by the bights 22 at one end of the hank of flexible biocompatible material 21. Abutment means for a tensioning tool 33, for pulling the tail 25 of the strand material, takes the form of a hole 34 located between the flat and round hook portions 31, 32, which hole is engaged by a spigot 35 at one end of a shank 36 of the tensioning tool. This tool 33 is in the form of a capstan with handgrip means 37 at the other end of the shank for rotating the capstan, a cleat 38 being provided on one side of the shank for securing the tail 25 of the strand material 21 to the shank for winding thereon upon rotation of the capstan. FIG. 6 shows the crimpable sleeve-like element 26 crimped on to the hank.

FIG. 7 shows a hooking member 39 having a broad flat yoke 40 with a round hook portion 32 integrated with and oppositely directed to each end of the yoke. Two such hooking members may have their yokes hooked on to spinous processes (not shown) of adjacent vertebrae, and two hanks and two crimpable sleeve-like elements combined therewith by hooking the bights 22 of the hanks on the round hook portions 32, with one hank on each side of the spinous processes, and the elements 26 crimped on to the hanks after they have been tensioned. Alternatively, one such hooking member 39 may have its yoke hooked on a spinous process of one vertebra while two hooking members 30 have their broad flat hook portions hooked on the lamina of an adjacent vertebra, and combined with two hanks and two crimpable sleeve-like elements by hooking the bights of the hanks on respective round hook portions on the hooking members 30, 39.

It will be appreciated that because the crimpable sleeve-like element 26 in FIGS. 5 and 6 encircles four lengths of the strand material 21, its bore must be of an adequate diameter for easy feeding of the tail 25 repeatedly therethrough, and—in consequence—the outside diameter will be commensurately larger. Preferably, therefore, as shown in FIGS. 1 and 2, FIGS. 3 and 4, and FIGS. 11 and 12, the crimpable sleeve-like element 26 encircles only the overlapping end lengths 27 of the strand 21, thus minimising the cross-sectional dimensions of the element 26. Thus the element 26 may be manufactured as an initially cylindrical and, preferably, internally screwthreaded sleeve, which then flattened slightly to give the preferred form shown FIGS. 8 to 10 with the turns of the internal screwthread 41 constituting circumferentially extending ribs, to enhance the grip on the strand material 21 upon crimping of the element 26 thereon.

Figure 11:
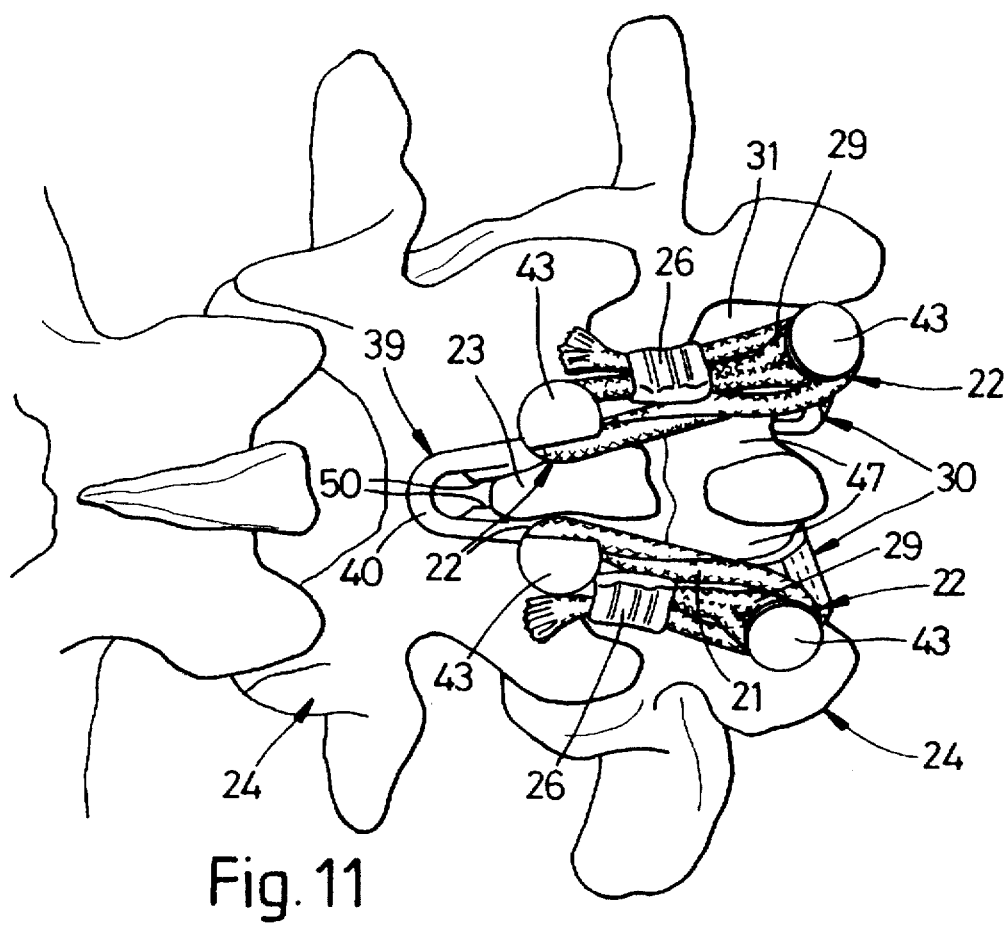
FIG. 11 is a plan view showing the two sets of components as in FIGS. 8 to 10, together with a preferred form of yoke and a pair of other hooking members of preferred form applied to adjacent vertebrae.
Figure 12:
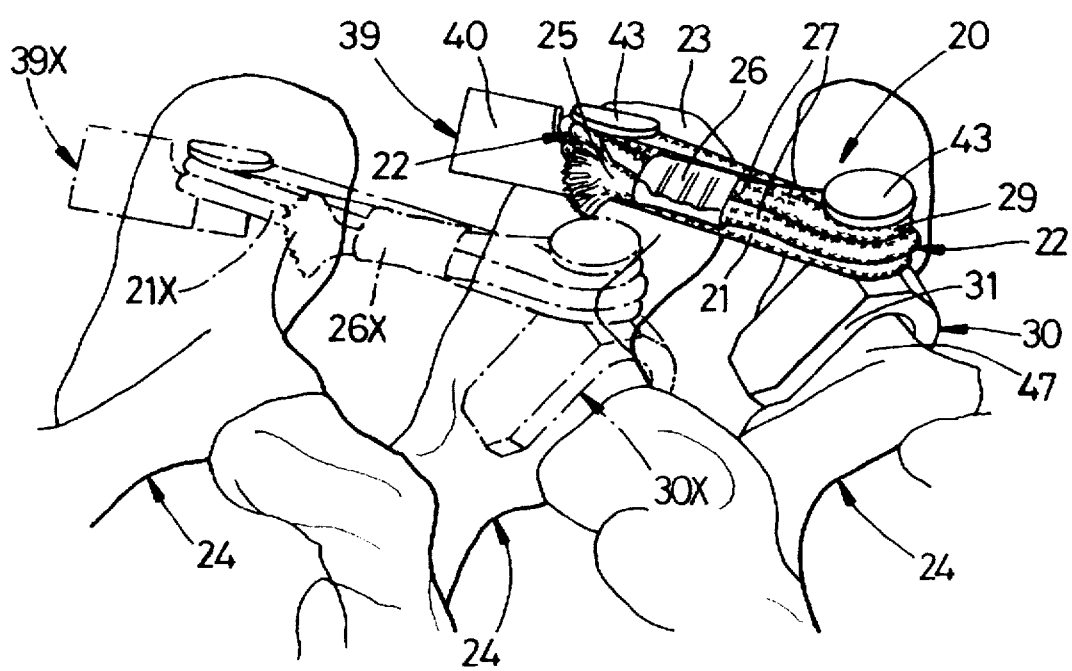
FIG. 12 is a side elevation of parts of FIG. 11, with an indication of similar surgical implants, yoke and other hooking members extending from one of the vertebrae to the next.
Figure 16A:
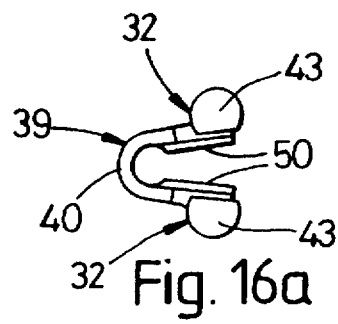
FIGS. 16(a), (b), (c) and (d) are respective plan, side, underneath and end views of the other hooking member shown in FIGS. 11 and 12.
Figure 16B:
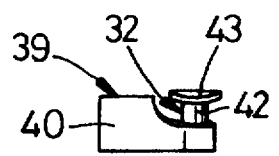
Figure 16D:
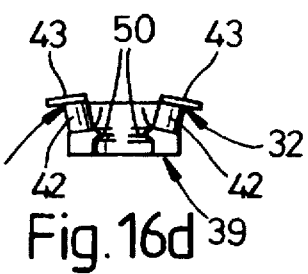
Figure 16C:
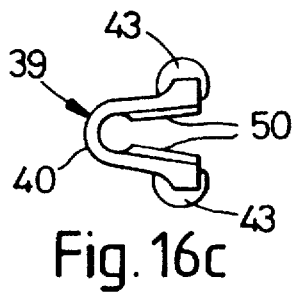

The preferred forms of crimpable sleeve-like element 26 and strand material 21 with eye 29 are shown in FIGS. 11 and 12 in use in combination with preferred forms of hooking members, details of which will be described with reference to FIGS. 13(a) to (d) and 16(a) to (d). In these preferred forms of hooking members the round hook portions 32 are formed by bollards having cylindrical bodies 42 and flat circular heads 43, and the heads on the hooking members 30 are shown in FIGS. 11 and 12 aiding retention of the eyes 29 of hanks of strand material hooked on the bollards.

In FIG. 14 the bollard 32 of one of the hooking members 30 is shown engaged by a forked end 44 of an applicator tool 45 having a striking portion 46 at the other end, which enables the hooking member 30 to be hammered into place on the lamina 47 at one side of the spinous process 23 of one vertebra 24, and—as shown in FIG. 11—another hooking member 30 is hammered into place on the lamina 47 at the other side of that spinous process 23. As can be seen in FIGS. 13(a) to (d), the inside of each broad flat hook portion 31 is provided with a sharp-ridged rib 48 extending in the direction of application of the hooking member 30, to enhance the grip on the engaged bone part. A leading end 49 of each broad flat hook portion 31 is provided with a chisel edge, to effect some shaving of the engaged bone part, if necessary, to achieve a good fit.

In FIGS. 16(a) to (d) a hooking member 39 can be seen to be provided with sharp-ridged ribs 50 extending along the insides of the arms of the yoke portion 40 in the direction of application to the spinous process 23 of an adjacent vertebra 24 in FIGS. 11 and 12, to enhance the grip on this engaged bone part.

Referring again to FIGS. 11 and 12 the bights 22 of hanks are applied to respective bollard type round hook portions on the yoke 39, 40, with the crimpable sleeve-like elements 26 encircling the overlapping end lengths 27 of the strands, and after tensioning of the strands (as by means of the tool shown in FIGS. 17 and 18, and which will be described presently) the elements 26 are crimped on to the lengths of strand passing therethrough to secure the strands in their tensioned state.

Figure 17:
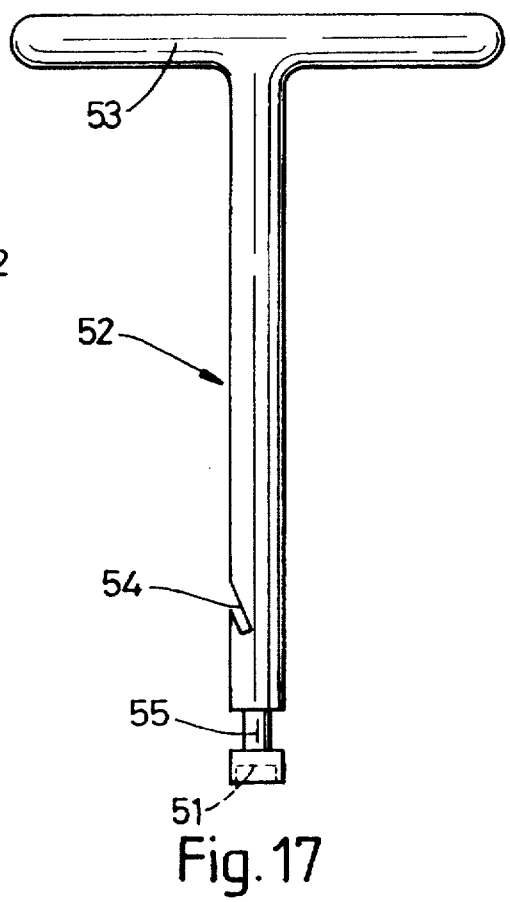
FIG. 17 is a side elevation of a tensioning tool for engagement with one of the hooking members shown in FIGS. 11 and 12.
Figure 18:
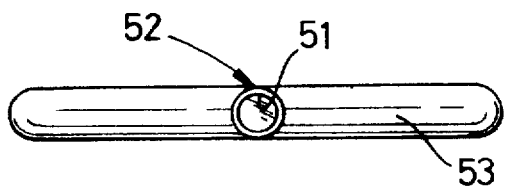
FIG. 18 is an underneath view of the tensioning tool shown in FIG. 17.

Any suitable one of the heads 43 of the bollard type round hook portions of the hooking members 30, 39 may serve as a spigot engageable by a socket 51 in one end of the tensioning tool 52 shown in FIGS. 17 and 18, the other end of which has a handgrip 53 enabling the tool to be rotated with the socket 51 thus engaged with a head 43. The tool 52 has a notch 54 into which the tail 25 of a hank can be jammed, and a neck 55 round which the strand material 21 can be wound as the tool is rotated to tension the strand material.

Further hooking members 30X, 39X, a hank of strand material 21X and crimped element 26X are indicated in chain dotted lines FIG. 12 providing further stabilisation between the vertebra carrying the hooking member 39 and the next adjacent vertebra.

We claim:

1. A surgical implant (20) comprising a hank formed from a single strand (21) of flexible biocompatible material with at least one bight (22) at each end of the hank, a tail (25) extending from at least one end, and at least one crimpable sleeve-like element (26) encircling part of the hank intermediate the bights (22), characterized in that the sleeve-like element (26) is formed of ductile material and encircles at least overlapping end lengths (27) of the strand, and further characterized by a pair of hooking members (30), each having a broad flat hook portion (31) for engaging one part of the spinal column, integrated with an oppositely directed and reverse facing round hook portion (32) engageable with the bight or bights (22, 29) at one end of the hank.

2. A surgical implant as in claim 1, characterized in that at least one of the hooking members (30) has abutment means (34) for a tensioning tool (33) for pulling the tail (25) of the strand material (21).

3. A surgical implant as in claim 2, characterized in that the abutment means (34) takes the form of a hole located between the flat and round hook portions (31, 32).

4. A surgical implant as in claim 1, characterized in that each round hook portion (32) is formed by a bollard having a cylindrical body (42) and a flat circular head (43).

5. A surgical implant as in claim 1, characterized in that a selection of hooking members (30,39) is made available with a variety of widths and radii of the broad flat hook portions (31) and/or of the yoke portion (40).

6. A surgical implant as in claim 1, characterized in that the insides of the broad flat hook portions (31) and/or of the broad flat yokes (40) are provided with sharp-ridged ribs (50) extending in the direction of application of the hooking members, to enhance the grip on engaged bone parts.

7. A surgical implant as in claim 1, characterized in that a leading end (49) of each broad flat hook portion (31) is provided with a chisel edge, to effect some shaving of an engaged bone part.

8. A surgical implant as in claim 1, characterized in that the hooking members (30, 39) are coated with hydroxyapatite to encourage ingrowth of bone tissue.

9. A surgical implant (20) comprising a hank formed from a single strand (21) of flexible biocompatible material with at least one bight (22) at each end of the hank, a tail (25) extending from at least one end, and at least one crimpable sleeve-like element (26) encircling part of the hank intermediate the bights (22), characterized in that the sleeve-like element (26) is formed of ductile material and encircles at least overlapping end lengths (27) of the strand, and further characterized by two hooking members (39), each in the form of a broad flat yoke (40) with a round hook portion (32) integrated with and oppositely directed to each end of the yoke, combined with two said hanks and two said ductile crimpable sleeve-like elements (26) respectively.

10. A surgical implant (20) comprising a hank formed from a single strand (21) of flexible biocompatible material with at least one bight (22) at each end of the hank, a tail (25) extending from at least one end, and at least one crimpable sleeve-like element (26) encircling part of the hank intermediate the bights (22), characterized in that the sleeve-like element (26) is formed of ductile material and encircles at least overlapping end lengths (27) of the strand, and further characterized by one hooking member (39) in the form of a broad flat yoke (40) with a round hook portion (32) integrated with and oppositely directed to each end of the yoke, and pair of hooking members (30), each having a broad flat hook portion (31) for engaging one part of the spinal column, integrated with an oppositely directed and reverse facing round hook portion (32) engageable with the bight or bights (22, 29) at one end of the hank.

11. A surgical implant (20) comprising a hank formed from a single strand (21) of flexible biocompatible material with at least one bight (22) at each end of the hank, a tail (25) extending from at least one end, and at least one ductile crimpable sleeve-like element (26) encircling at least the tail and an other part of the hank within the sleeve-like element, the inside of the sleeve-like element being provided with circumferentially extending ribs (41) to enhance the grip on the encircled strand material, characterized in that the ductile crimpable sleeve-like element (26) is manufactured as an initially cylindrical and internally screwthreaded sleeve, which is then flattened slightly, so as to accommodate a pair of overlapping end lengths (27) of strand material (21) in an element having minimal cross-sectional dimensions.

12. A method of spinal stabilization comprising securing to two parts (23) of the spinal column respective bights (22) at the ends of a hank formed from a single strand (21) of flexible biocompatible material having part of the hank intermediate the bights encircled by at least one crimpable sleeve-like element (26), with a tail (25) of the strand (21) extending from an end of the hank, and pulling the tail (25) to take up slack in the hank and tension the strand (21), characterized in that the crimpable sleeve-like element is formed of ductile material and is squeezed on to the lengths of strand passing therethrough to secure the strand in its tensioned state, and in that excess strand material (21) is then cut off;

and further characterized in that hooking members (39), each having a broad flat yoke (40) with a round hook portion (32) integrated with and oppositely directed to each end of the yoke, are applied one to each of two spinous processes (23), with the respective yoke portion (40) engaged with a spinous process (23), the round hook portions (32) then being engaged by respective bights (22) of a pair of hanks (20) each of which is formed from a single strand (21) of material, with a tail (25) and an encircling ductile crimpable sleeve-like element (26), the tails (25) being pulled, the ductile crimpable sleeve-like elements (26) squeezed, and excess strand material (21) cut off, as described above, to achieve symmetrical loading.

13. A method of spinal stabilization comprising securing to two parts (23) of the spinal column respective bights (22) at the ends of a hank formed from a single strand (21) of flexible biocompatible material having part of the hank intermediate the bights encircled by at least one crimpable sleeve-like element (26), with a tail (25) of the strand (21) extending from an end of the hank, and pulling the tail (25) to take up slack in the hank and tension the strand (21), characterized in that the crimpable sleeve-like element is formed of ductile material and is squeezed on the lengths of strand passing therethrough to secure the strand in its tensioned state, and in that excess strand material (21) is then cut off;

and further characterized in that a hooking member (39) having a broad flat yoke (40) with a round hook portion (32) integrated with and oppositely directed to each end of the yoke is applied to the spinous process (23) of one vertebra (24), and two hooking members (30) each having a broad flat hook portion (31) integrated with an oppositely directed and reverse facing round hook portion (32) are applied to the lamina (47) at both sides of the spinous process (23) of another vertebra (24), the respective round hook portions (32) of the yoke (40) and the corresponding hooking members (30) engaged with the lamina (47) then being engaged by respective bights (22) of a pair of hanks (20) each of which is formed from a single strand (21) of material, with a tail (25) and an encircling ductile crimpable sleeve-like element (26), the tails (25) being pulled, the ductile crimpable sleeve-like elements (26) squeezed, and excess strand material (21) cut off, to achieve symmetrical loading.

14. A method of spinal stabilization comprising securing to two parts (23) of the spinal column respective bights (22) at the ends of a hank formed from a single strand (21) of flexible biocompatible material having part of the hank intermediate the bights encircled by at least one crimpable sleeve-like element (26), with a tail (25) of the strand (21) extending from an end of the hank, and pulling the tail (25) to take up slack in the hank and tension the strand (21), characterized in that the crimpable sleeve-like element is formed of ductile material and is squeezed on to the lengths of strand passing therethrough to secure the strand in its tensioned state, and in that excess strand material (21) is then cut off;

and further characterized in that hooking members (30), each having a broad flat hook portion (31) integrated with an oppositely directed and reverse facing round hook portion (32), are applied one to each of two vertebrae (24), with the respective flat hook portion (31) engaged with the spinous process (23) or to the lamina (47) or transverse process at one side of the spine, then engaging the bights (22) of the hank with the respective round hook portions (32) of the hooking members (30), prior to the tail (25) of the strand (21) being pulled, and excess strand material (21) cut off.

15. A method as in claim 14, characterized in that a similar combination of hooking members (30), hank (20) and ductile crimpable sleeve-like element (26) is applied similarly at the other side of the spine to achieve symmetrical loading of the vertebrae (24).

16. A method as in claim 14, characterized in that a tensioning tool (33) is applied to one of the hooking members (30), engaged with the tail (25) of the respective hank (20) and operated to tension the strand (21) before squeezing of the ductile crimpable sleeve-like element (26).

* * * * *